United States Patent
Silbergleit et al.

(10) Patent No.: US 8,035,811 B2
(45) Date of Patent: Oct. 11, 2011

(54) DEVICES AND METHODS FOR VISUALIZATION OF A SAMPLE IN A MICROPLATE

(75) Inventors: Arkadiy Silbergleit, Escondido, CA (US); Adrian Fawcett, Carlsbad, CA (US); Michael Andrew Swartz, San Diego, CA (US); Kevin Daley Simmons, San Diego, CA (US)

(73) Assignee: Helixis, Inc., Carlsbad, CA (US)

( * ) Notice: Subject to any disclaimer, the term of this patent is extended or adjusted under 35 U.S.C. 154(b) by 6 days.

(21) Appl. No.: 12/564,832

(22) Filed: Sep. 22, 2009

(65) Prior Publication Data

US 2010/0103410 A1     Apr. 29, 2010

Related U.S. Application Data

(60) Provisional application No. 61/099,166, filed on Sep. 22, 2008.

(51) Int. Cl.
*G01N 1/10* (2006.01)
(52) U.S. Cl. ...................................................... 356/246
(58) Field of Classification Search ............. 356/246
See application file for complete search history.

(56) References Cited

U.S. PATENT DOCUMENTS

| | | | |
|---|---|---|---|
| 3,356,462 A | 12/1967 | Cooke et al. | |
| 4,772,487 A | 9/1988 | Gotoh et al. | |
| 5,683,648 A * | 11/1997 | Fortin | 264/550 |
| 5,910,287 A | 6/1999 | Cassin et al. | |
| 6,051,191 A | 4/2000 | Ireland | |
| 2005/0052646 A1 | 3/2005 | Wohstadter et al. | |
| 2007/0211245 A1 | 9/2007 | Pastel et al. | |
| 2008/0165353 A1 | 7/2008 | Kataoka | |
| 2009/0010811 A1 * | 1/2009 | Chan et al. | 422/102 |

OTHER PUBLICATIONS

PCT/US09/57909 Search Report dated Oct. 28, 2009.

* cited by examiner

*Primary Examiner* — Roy M Punnoose
(74) *Attorney, Agent, or Firm* — Knobbe, Martens, Olson & Bear, LLP

(57) ABSTRACT

Disclosed herein is a microplate comprising a plurality of wells and methods and systems comprising such microplates, wherein an individual well comprises an opaque or non-transparent surface at or near the bottom of the well. The microplates herein can provide improved visualization of the process of filling a well with a liquid reagent. The microplates can be configured to perform chemical analysis, such as polymerase chain reaction (PCR) or nucleic acid detection.

18 Claims, 6 Drawing Sheets

DEVICES AND METHODS FOR VISUALIZATION OF A SAMPLE IN A MICROPLATE

CROSS-REFERENCE

This application claims the benefit of U.S. Provisional Application No. 61/099,166, filed Sep. 22, 2008, which application is incorporated herein by reference.

BACKGROUND OF THE INVENTION

Many chemical reactions and analyses were original performed in test tubes. When running a series or multiple chemical analyses, the number of test tubes can become burdensome as well as requiring a significant amount of sample. Microplates with an array of wells where developed to perform multiple reactions and analyses in a single container.

Polymerase Chain Reaction (PCR) thermal cycling is most frequently performed in conical plastic wells arrayed in the form of microplates. PCR microplates are typically colorless or lightly tinted with color and because the PCR solution is also colorless it is typically quite difficult to identify which wells are full and which are empty. When plates are being manually loaded with reaction mix, it is very easy for the user to inadvertently load two samples into one well causing defective reactions or load a sample into an incorrect location potentially causing erroneous experimental conclusions to be drawn. This issue is especially apparent as smaller plates are employed. The smaller plates allow for reactions to be carried out in small volumes, but the smaller dimensions increase the difficulty of visualizing the filling of the wells.

There is a need in the art for a device and system to easily distinguish empty and full wells in order to dramatically reduce manual filling errors of a microplate.

SUMMARY OF THE INVENTION

One aspect of the invention is a microplate comprising: a body and a plurality of wells, each comprising a bottom and a sidewall, wherein the sidewall is at least partially transparent and wherein the bottom comprises an opaque region.

In some embodiments, the bottoms of the wells have a substantially horizontal portion, and wherein the opaque region is confined to such substantially horizontal portion. In some embodiments, the plurality of wells are configured to contain a liquid such that when viewed from the openings of the plurality of wells, the opaque region has a different appearance for wells containing liquid than for the wells that do not contain liquid.

In some embodiments, the bottom of the wells comprise an inner surface and an outer surface, and wherein the opaque region is on the outer surface. In some embodiments, the opaque region comprises a black dot on the outer surface. In some embodiments, the opaque region is printed onto the outer surface. In some embodiments, the inner surface is textured.

An aspect of the invention is a system comprising: a microplate comprising: a body and a plurality of wells, each comprising a bottom and a sidewall, wherein the sidewall is at least partially transparent and wherein the bottom comprises an opaque region; and an illumination device configured to receive the microplate such that light from the illumination devices is passed through the wells of the microplate allowing optical detection of the opaque region.

In some embodiments, the illumination device comprises a body, a light source, and an illumination surface, wherein the light source illuminates the illumination surface and wherein the illumination surface is configured to be positioned under the microplate when received. In some embodiments, the system further comprising a holder, wherein the holder is configured to hold the microplate and the illumination device is configured to receive the holder and the microplate.

In some embodiments, the holder is configured to fit into a centrifuge for microplates.

An aspect of the invention is a method comprising: obtaining a microplate comprising a body and a plurality of wells comprising a bottom and a sidewall, wherein the sidewall is at least partially transparent and wherein the bottom comprises an opaque region; adding a liquid to at least one of the wells; observing a well from above the microplate; and determining whether or not liquid has been added to such well by observing the appearance of the opaque region.

In some embodiments, the observing of the appearance of the opaque region is performed by a person. In some embodiments, the observing of the appearance of the opaque region is performed by an instrument.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Many novel features of the invention are set forth with particularity in the appended claims. A better understanding of the features and advantages of the present invention will be obtained by reference to the following detailed description that sets forth illustrative embodiments, in which many principles of the invention are utilized, and the accompanying drawings of which:

DETAILED DESCRIPTION OF THE INVENTION

Figure 1:
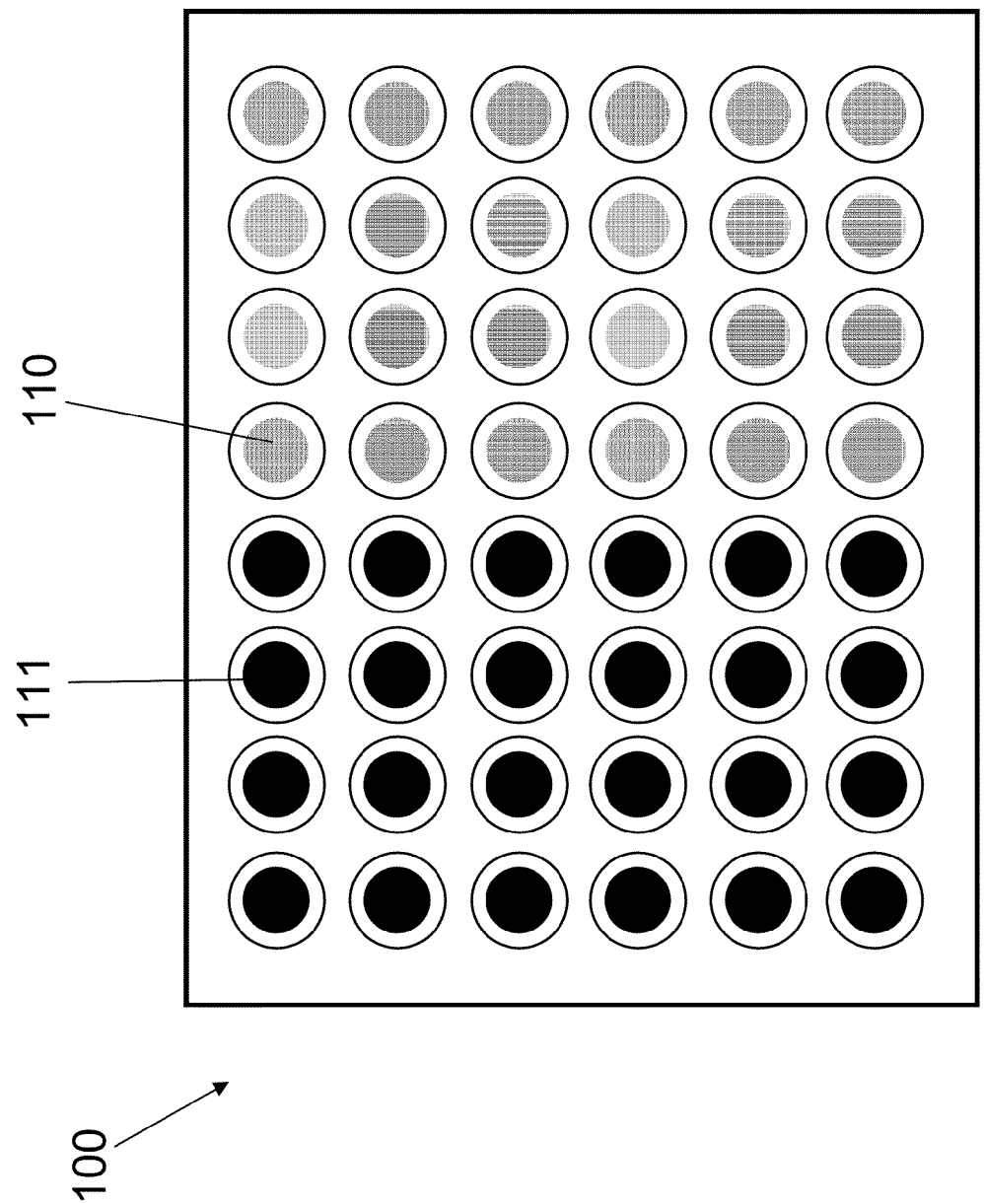
FIG. 1 shows an exemplary microplate of the invention, visualized from above, wherein some wells (the wells on the left) have liquid in them, and some wells (the wells on the right) do not have liquid in them.

Disclosed herein is a microplate comprising a plurality of wells and methods of using such microplates, wherein an individual well comprises an opaque or non-transparent surface at or near the bottom of the well. For example, a microplate can comprise 48, 96, 384, or more wells. The microplate can be a microplate as is known or standard in the art, with an improvement comprising an opaque region at the bottom of the wells of the microplate. A microplate can be configured to perform chemical analysis, such as polymerase chain reaction (PCR) or nucleic acid detection. In some embodiments, at least some of the wells comprise reagents for performing a chemical analysis. For example, a well can contain dried PCR reagents, such as a set of primers.

A microplate can be a flat plate with a plurality of wells. The wells can be configured to contain a chemical reactant or a chemical reaction, or a fluid of any kind Microplates have become a standard tool in analytical research and clinical diagnostic testing laboratories. An exemplary method of using a microplate is to conduct an ELISA assay to identify analytes in a fluid. In another exemplary method, a microplate is used for polymerase chain reaction (PCR) for amplifying and/or detecting nucleic acids sequences.

A microplate can have 2, 6, 24, 48, 96, 384, 1536, 3456, 9600 or more wells. The size and shape of the microplate can vary greatly as is known in the art. The layout of the wells can also vary greatly, for example, many microplates have a plurality of wells arranged in a 2:3 rectangular matrix. Other microplates have a plurality of wells arranged in a 1:1 or 3:4 matrix. A microplate as described herein can have any layout of wells as would be obvious to one skilled in the art.

Microplates can have open-top wells, cups or recesses capable of containing small volumes of typically aqueous samples ranging from fractions of a microliter to hundreds of microliters. In some instances, microplates include sample well arrays totaling 96 sample wells that are arranged in an array of 8 by 12 sample wells and have center-to-center well spacing of 9 mm, such as the multi-well plate disclosed in U.S. Pat. No. 3,356,462. In an embodiment, a microplate includes arrays of 384 wells arranged in 16 by 24 array with a reduced center-to-center well spacing of 4.5 mm. Microplates are not limited to any particular number of wells nor to any specific array pattern. For example, U.S. Pat. No. 5,910,287 discloses a microplate comprising a well array of more than 864 wells. In an embodiment, a microplate includes arrays of 48 wells in a 6 by 8 array with a center-to-center spacing of 4.5 mm.

An individual well of a microplate can generally contain a volume of fluid of between about 1 nanoliter and several milliliters. In an example a well comprises is configured to contain 1 µL to about 100 µL, in some embodiments the wells are configured to contain 3 µL to about 50 µL, in some embodiments the wells are configured to contain about 5 µL to about 20 µL. The wells can be configured to contain a dry, solid, or liquid reagent or reactant. In many instances, wells have a circular or square opening on the surface of the microplate, however, a microplate herein can have wells with a surface area with any shape.

Wells can be formed on either the top or bottom surface or both surfaces of a microplate substrate. A well can be a space having a width, a depth, and an opening surrounded by a sidewall and a bottom surface. The opening of a well can be any shape for example substantially round, square, oval, rectangular, hexagonal, crescent, or star-shaped. The well can be any shape for example substantially round, square, oval, rectangular, hexagonal, crescent, or star-shaped. In one embodiment, the well is circular or cylindrical.

The bottom and the sidewall connect to form the bottom corner of the wells at the junction where the bottom and sidewall are joined. The angle at which the sidewall and bottom are connected can be substantially 90 degrees around the perimeter of the bottom or alternatively, the angle can vary from less than 90 degrees to greater than 90 degrees around the perimeter of the bottom. The connection between the bottom and sidewall can be continuous around the perimeter of the bottom. Alternatively, in some embodiments, the connection between the bottom and the sidewall is not continuous around the perimeter of the bottom.

The sidewall of the well can be any shape. For example, the sidewall can be cylindrical in shape and connected to a round bottom. The sidewall of the well can also have multiple sides for example, the sidewall of a well with a hexagonal-shaped bottom has six sides which make up the sidewall of the well. The sides of the well which make up the sidewall are continuous or alternatively, the sides are discontinuous. For example, in a hexagonal shaped reaction chamber, wells can be closed, such that the sides are continuous and connect to each other or the wells can be open, such that the sides are not continuous and do not connect to each other. The sidewall can have a smooth surface or an irregular surface.

A microplate as described herein can comprise a substrate comprising wells, such as individual reaction chambers. In many instances, a microplate comprises a plurality of wells, as is suitable for the chemical reaction to be performed within the wells. The size of the microplate and the plurality of wells can depend on the composition and end use of the microplate. An individual well can comprise a bottom and sidewall. A well can comprise an opening at the top of the well, a sidewall, and a bottom surface. The surfaces can be flat or curved or any shape as is suitable to those skilled in the art. The sidewall can be angled in the microplate, for example, according to American National Standards Institute (ANSI) standards. In some instances, the sidewall is angled at 17 to 18.5 degrees. In an embodiment, the sidewall is angled at 17.5 degrees. In many instances as described herein, the sidewall and substrate of the microplate comprises a transparent or partially-transparent material. The transparent material can have a color or a tint. A bottom surface of a well of the microplate can comprise an opaque region. The opaque region is often on the outer surface of the well. The opaque region can be embedded in material composing the microplate. For example, an opaque region can be molded or injected into a material of the microplate. In an embodiment, a microplate herein comprises 48 wells with a center-to-center well spacing of 4.5 mm arrayed in a 6 by 8 well matrix, wherein each well comprises an opaque region at or near the bottom surface of the well.

A common issue when manually filling a microplate with liquid is the user inaccurately keeping track of which wells are filled with the liquid and which wells are empty. Many higher density microplates (such as a 384-well) plate, are filled automatically by a robot. However, when filled by a human, for example, under a hood at a laboratory bench, it can be difficult to see a colorless or near colorless liquid in a transparent microplate. In many instances, a microplate is transparent in order to provide better optical detection properties for monitoring a reaction with the plurality of wells of the microplate. As described, a microplate is provided herein with a plurality of wells, wherein an individual well comprises an opaque region, for example at the bottom of the well, that changes in appearance when viewed by the eye of a human when filled with liquid as discussed further herein.

In some embodiments, an opaque region of a well can be viewed by the eye of a human 680 (FIG. 6) without the aid of an instrument 690 (FIG. 6) or an automatic optical detection system. In some instances, the opaque region appears less dark to the naked eye when dry. When fluid is placed in a well, the surface appears darker. This can be due to the optical properties of the well and the diversion of light. When the microplate is backlit, for example, by an illumination source, the contrast of the opaque region can be more apparent.

An opaque region can have any color that can be discerned by the human eye or by a detector. In some cases, the opaque region can be translucent, in other cases the opaque region is completely opaque, transmitting little or no light. Generally dark colors can be used. In an embodiment, the opaque region is black.

A well can have a bottom and a sidewall which define the boundary of the reaction chamber. The bottom of the well can be any shape for example substantially round, square, oval, rectangular, hexagonal, crescent, or star-shaped. The bottom of the well can be planar, concave or convex. The bottom of the well is opposed to the opening of the reaction chamber. As described herein the bottom of the well can have an opaque region. In many embodiments, the opaque region is the outer surface of the bottom of the well, away from the opening. The opaque region can consist of a different material than the microplate, for example paint versus a plastic, and be on the outside surface of the bottom of the well in order to avoid reacting with any reactant contained within the well. Also, the thickness of the material that creates the well can vary. In some embodiments, the thickness of the bottom is similar to the thickness of the sidewall. In other embodiments, the thickness of the bottom is different than the thickness of the sidewall. The thickness of the bottom can be related to the optical properties of the material composing the well. For example, when no liquid is in the well, the thickness of the bottom can be such that the opaque region is visually diminished or more dim. When liquid is in the well, the opaque region becomes more clearly visible due to the optical properties of the liquid or the optical properties of the material composing the well.

In some instances, the opaque region can be coated, marked, or painted onto a surface of the well. For example, an opaque dye, ink, or paint can be painted onto the bottom surface of a well. In many instances, the opaque region is the outer surface of the well. An opaque region can be printed onto a bottom surface of a well. In some embodiments, the opaque region of a plurality of wells is provided to the wells at the same time, for example in a printing process. In another embodiment, the opaque regions are provided to the wells in series. A pad printing process can be used to place the opaque region on the plurality of wells. A transfer film can be used to manufacture the opaque region. A heated ink delivery process can also be used.

In some embodiments, the opaque region can represent a different material formulation than the material of the sidewalls and the rest of the plate. For example, the opaque region can be introduced by co-molding with an opaque polymer and a transparent polymer such that the opaque polymer is molded into the bottom portion of the well creating the opaque region.

In some embodiments, the opaque region comprises the inner surface of the well. Generally, the bottom of the well has the opaque mark and the sidewalls do not. In some embodiments, the sidewalls of a well are also coated or painted with an opaque mark. Examples of materials that can be utilized to create an opaque region include, but are not limited, ink, dye, paint, plastics, and the like. In an embodiment, the opaque region comprises a polymer, such as polypropylene. A polymer can be adhered to a surface of a well by melting. In an embodiment, the opaque region comprises a material that becomes more opaque when contacted with a liquid, such as water. In an embodiment, the opaque region comprises a material that is not opaque unless contacted with a liquid.

An exemplary microplate as described herein is demonstrated in FIG. 1, wherein the microplate 100 comprises a 6 by 8 array of 48 wells 110. The wells 110 of the microplate 100 comprise an opaque region at the bottom of the well 110, which is contrasted with the transparent or partially transparent microplate 100. The wells are generally visualized from above as shown. When unfilled, the opaque regions of the wells 110, can be seen. The exemplary microplate 100 can be placed against a white background and illuminated from above, or the microplate can be illuminated from below with an illumination device as described herein. When a well 110 is filled with a liquid 111, the contrast of the opaque region of the well can increase as demonstrated by the liquid-filled wells 111 in the exemplary FIG. 1. In this manner, the user can know when a well 110 of the microplate 100 is filled with a liquid 111, reducing filling errors made manually in a laboratory. The contrast can also be used to verify a microplate 100 filled by an automatic device.

The opaque region can be on the outer surface of a well of a microplate, for example by printing, as described herein. In some instances, the opaque portion is generally limited to the bottom surface of the well, and generally does not extend up the side wall of the well. For example, the opaque portion is generally on the substantially horizontal portion of the well, but is generally not on the substantially vertical portions of the well. For example, if the microplate comprises 20 μl wells by volume as arrayed in a typical for a 384-well microplate, the opaque region may be about 1.5 mm in diameter. In some embodiments, the opaque region is not greater than 2 mm in diameter. The opaque region can have a diameter of about 0.1 mm to about 5 mm in diameter. When working with an optical detection system other than the human eye, the opaque region can be smaller in diameter than 0.1 mm. The size of the opaque region can vary according to the size of the well or the volume the well can contain. In many instances, the opaque region occupies almost an entire substantially horizontal surface of a bottom of well. In other instances, the opaque region occupies 10%, 20%, 30%, 40%, 50%, 60%, 70%, 80%, 90% or more of the substantially horizontal surface of a bottom of a well.

In an embodiment, the opaque region does not extend to the sidewall of a well. In some instances, the opaque region extending to the sidewalls of the well can obscure the desired optical effect of achieving greater contrast when a well is filled with liquid. In an embodiment wherein a well bottom is flat, the opaque region can extend to cover the entire flat surface. In many instances, a bottom of a well is slightly curved and the opaque region does not extend to any part of the well that is angled at more than 30 degrees from horizontal. Wells generally have an inner surface and an outer surface. Where the well has a gradual curve from the substantially horizontal bottom surface to the substantially vertical side surface, the opaque portion on the outer surface generally does not extend up the side wall any further than the point on the outer side wall that is at the height of the lowest point on the inner surface of the tube. That is, if a horizontal line is drawn at the lowest portion of the inner surface (the bottom of the inner portion of the tube), the opaque portion generally does not extend higher than the point where this horizontal line crosses the outer surface of the well.

A method is also provided herein that comprises adding a sample to a well of a microplate and visualizing the sample to determine whether or not the well has been filled, wherein the well comprises an opaque portion and a transparent portion. Often, when filling a microplate manually, it can be difficult for the user to manually view the sample in the well. For example, if a user is filling all 96 wells of a 96-well microplate, the user may lose track of how many or which wells he has filled. If some wells are not filled, or they are filled too full, it can create errors in the results of chemical analysis to be carried out in the wells. In a higher density microplate (such as a plate with about 4.5 mm center to center spacing, or a plate with about 9 mm center to center spacing) the volume contained within a well is often small, generally from about 0.2 μL to about 50 μL. With many prior art higher density microplates, the microplates are filled or have to be filled by a robot. Filling a well with a robot can improve the efficiency and accuracy of filling a well of a microplate, however, robotic filling can reduce the flexibility of the use of the microplate in laboratory procedures. While the methods of the invention are generally directed to manual filling, these methods can also be used for automated or robotic filling and for robotic visualization. The opaque marking provides a contrast between filled and unfilled wells that can be readily visualized by the human eye. This change in contrast can also be used to increase the ease of detecting whether or not wells are filled by an optical system utilizing, for example a photodetector.

Figure 2:
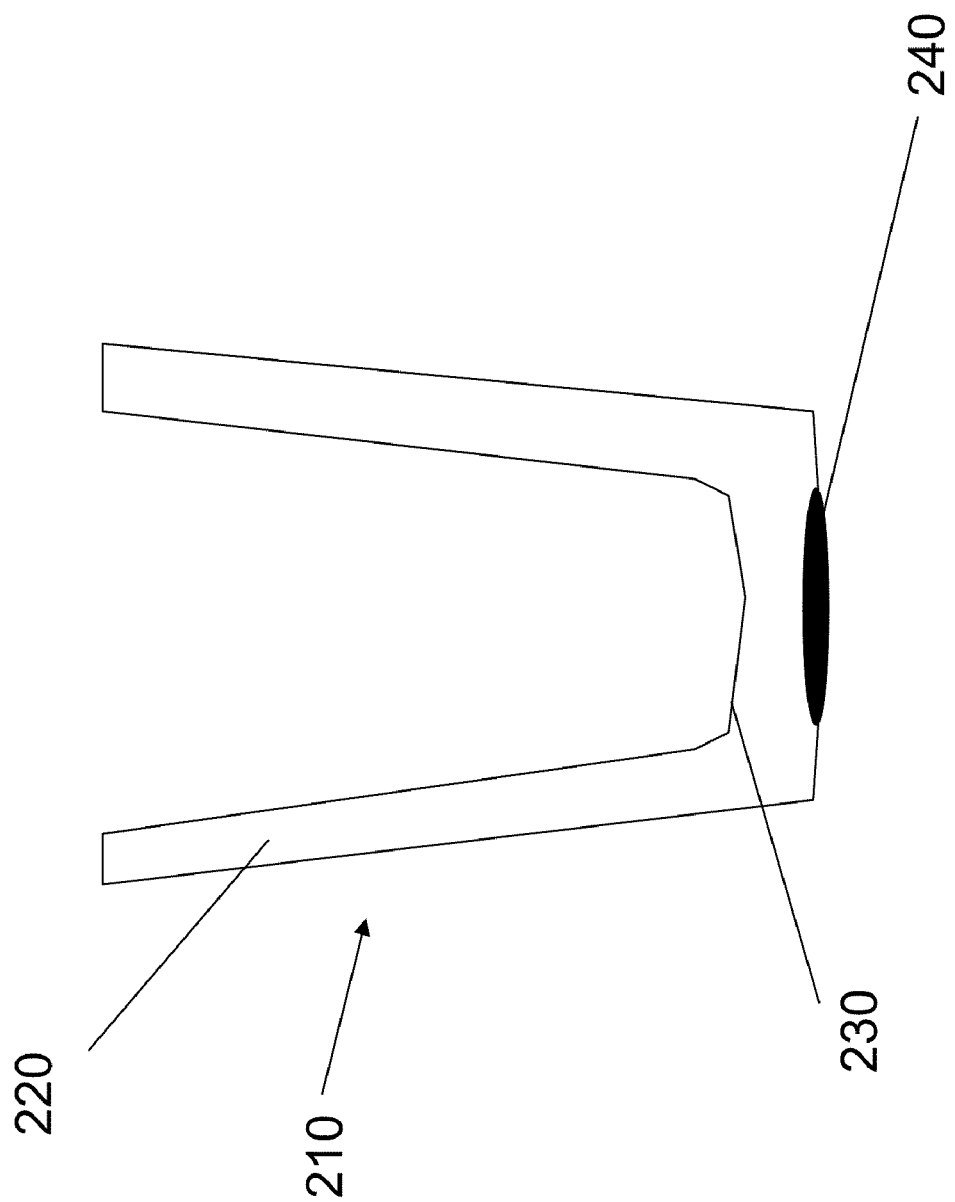
FIG. 2 shows an exemplary well of the invention having an opaque region on the bottom of the well.

FIG. 2 demonstrates an exemplary well 210 comprising an opaque region 240 as described herein. The well 210 has slightly sloped sidewalls 220 that are transparent or partially transparent. In this exemplary embodiment of FIG. 2, the opaque region 240 is on the outer bottom surface of the well 210 and does cover a sidewall 220. The inner surface 230 opposite the opaque region 240 can receive a liquid sample, and therefore increase the contrast of the well 210 when viewed from the opening as shown in the microplate 100 of FIG. 1.

In an embodiment herein, a microplate with a plurality of wells comprising an opaque region is filled with a robot or automated device, such as an automated pipette. However, when a microplate is not filled with a robot, the chances of manual error can increase.

When fluid is in a well of a microplate, the fluid can act as a lens to view the opaque region at the bottom of a well. When liquid is in a small volume well, such as those in a microplate as described, a convex meniscus may form that can act as a lens. The fluid can increase the contrast between a fluid-filled well with an opaque region as compared to a non-fluid-filled well.

Figure 4:
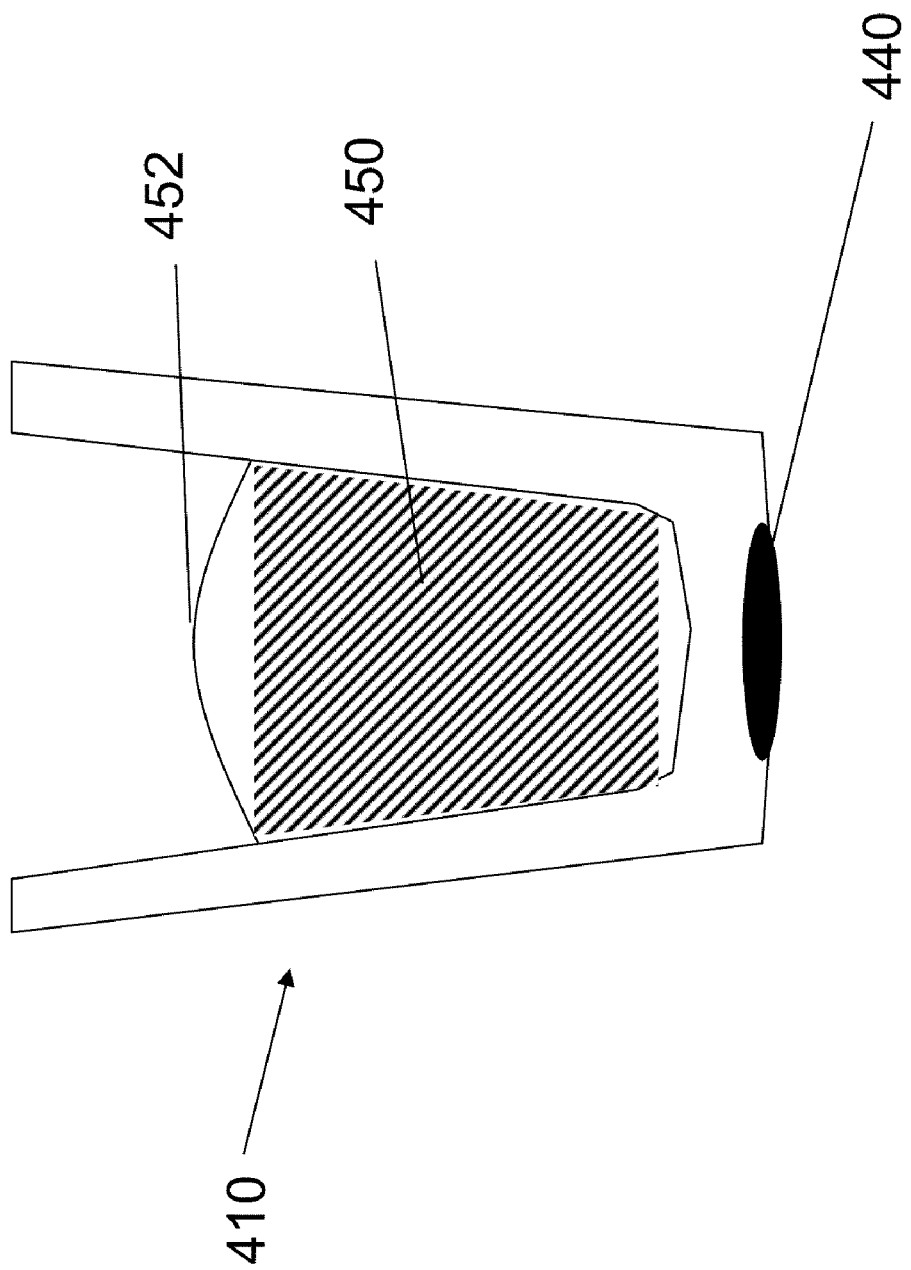
FIG. 4 shows an exemplary well of the invention having an opaque region on the bottom of the well wherein the well contains fluid.

FIG. 4 illustrates a well 410 containing a colorless or partially-transparent fluid 450. The fluid 450 has a meniscus 452 at the top due to the capillary action within the well 410. The meniscus 452 can act as a lens when the bottom of the well 410 is viewed from the opening of the well 410, thereby enhancing the contrast of the opaque region 440 of the bottom of the well 410 to the background of a transparent microplate, when the well 410 contains with a fluid 450. In this figure, the meniscus is shown as convex, as might be expected with a liquid that does not wet the surface of a well. It is understood that in some cases, for example where the fluid wets the surface of the well, the surface of the meniscus will be concave. Here as well, optical lensing effects can act to enhance the contrast between a filled and unfilled well having an opaque portion.

In an embodiment, a well of a microplate has a textured inner surface. The textured inner surface can divert or reflect light away from the opaque outer surface of the well. The textured inner surface can result in the scattering of light, acting to reduce the contrast of the opaque region of a well as compared to a well without a texture inner surface. When liquid is in contact with the inner surface, it reduces the amount of diversion of light from the texture (reduced scattering), and therefore the opaque region can become more clear when the liquid (such as a sample) is in a well of the microplate. For example, a textured surface can reduce the contrast of the well when not filled and when filled, can offer similar contrast to a non-textured well with an opaque region. The texture can be part of a film that coats the inner surface of a well of microplate. The texture can be molded into the microplate. A textured surface can be scratched into a well of a microplate. In some instances, the textured surface can be manufactured by sand blasting the bottom inner surface of a well. A textured surface may have no effect on any chemical reaction that is to be carried out within a well or alter the electrical properties of the well or the chemical reaction.

Figure 3:
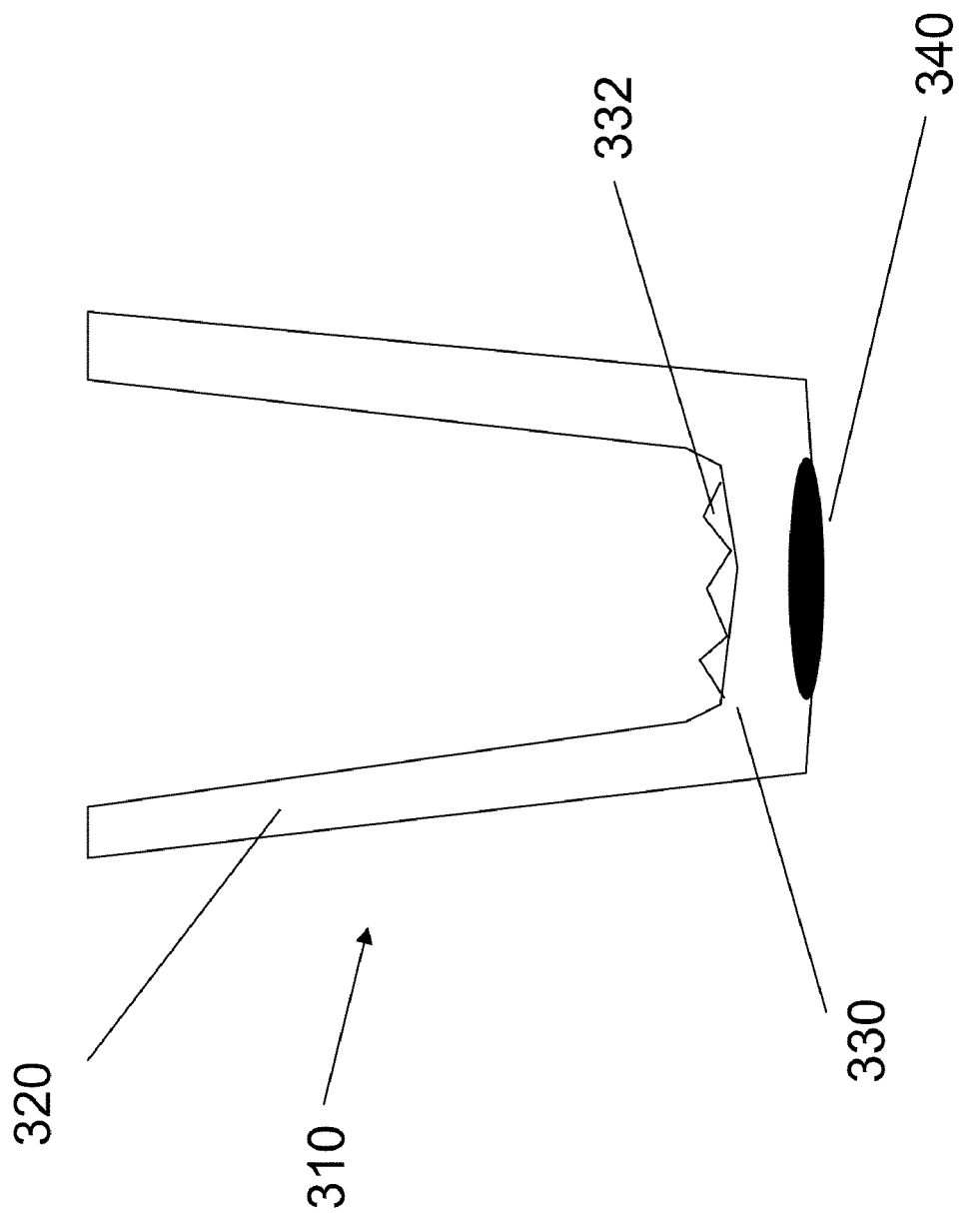
FIG. 3 shows an exemplary well of the invention having an opaque region on the bottom of the well, and a textured portion on the inside surface of the well.

FIG. 3 illustrates an exemplary well 310 with a textured surface 332 on the inner surface 330 of the well 310 opposite the opaque region. The texture surface 332 can scatter light and therefore when the bottom of the well 310 is viewed from the opening of the well 310, the contrast of the opaque region at the bottom of the well 310 is decreased. When the well 310 contains liquid, the liquid contacts the textured surface 332 and diminishes the scattering of the textured surface 332, therefore providing greater contrast of the opaque region when viewed from the opening. In the exemplary embodiment, the textured surface 332 does not occur on the sidewalls 320 of the well 310. In an embodiment, a well with a textured inner surface at the bottom of the well provides a greater contrast ratio of the opaque region in relation to filled versus and unfilled well as compared to a non-textured well.

In an embodiment, a texture can obscure the opaque region from view when the well is dry. When the well is filled with fluid, the wetting of the texture causes the texture to become more transparent and therefore makes the opaque region highly visible creating the appearance of the entire sample becoming colored or dark according to the color of the opaque region.

In some instances, a system is provided that comprises a microplate with a plurality of wells, an individual well comprising an opaque region at or near or at the bottom of the wells. The system further comprises an illumination device. For example, an illumination device can be any source that emits light, such as a backlight such as an electroluminescent lamp (for example, an indiglo illuminator). The illumination device can be attached or attachable to the microplate. In some embodiments, the illumination device is a table or platform with a light on which a microplate can rest. In other embodiments, the microplate can be mechanically coupled to the illumination device. In an exemplary embodiment, the illumination device is coupled to an adapter for placing the microplate in a centrifuge. In some instances, the illumination device can comprise a stage that can be angled toward a user.

Figure 5:
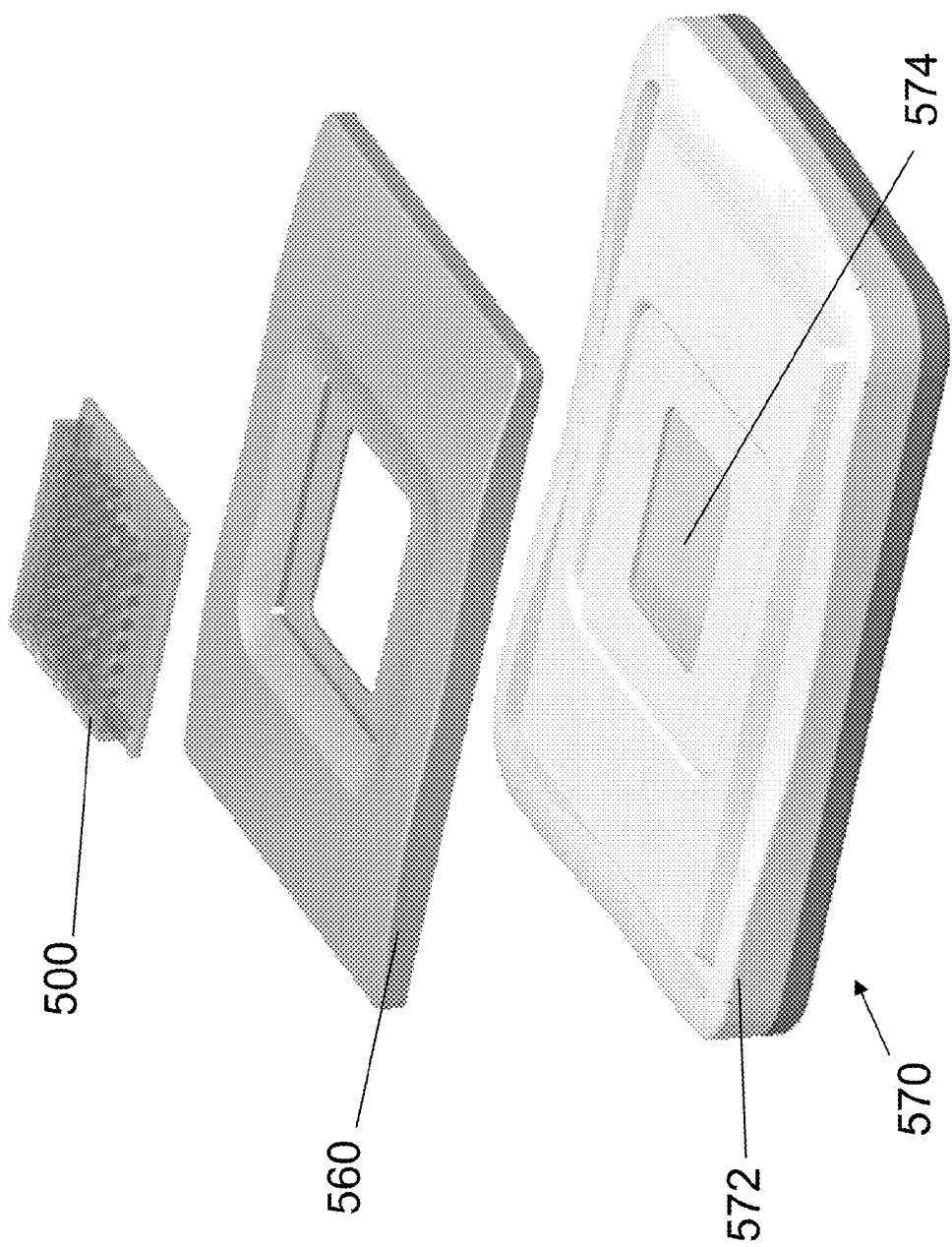
FIG. 5 shows an exploded view of an exemplary system of the invention comprising a plate, a plate holder, and an illumination device.

A system as described herein comprising a microplate 500, a holder 560, and an illumination device or illuminated base 570 is illustrated in FIG. 5. The microplate 500 comprises 48 wells with an opaque region at the bottom of each of the wells. The microplate 500 is configured to fit snugly into the holder 560. The holder 560 can be of the size and shape to fit into a standard centrifuge. Therefore, after a microplate 500 has been placed in the holder 560 and filled, the combined apparatus can be inserted into a centrifuge for ease of use. The illumination device 570 comprises a body 572 and an illuminated surface 574. The illuminated surface 574 in the exemplary embodiment of FIG. 5 corresponds to the footprint of the microplate 500. The illuminated surface 574 can be illuminated by a light source in the body 572 of the illumination device 570. The light source can be any light source as would be known to one skilled in the art. The illumination device 570 can comprise an electrical connection to power the light source and/or a battery. Other methods and systems of powering the illumination device 570 as would be obvious to one skilled in the art can be used in the illumination device 570 as described herein. The system as demonstrated in FIG. 5 can also comprises legs or a stand to angle the resting position of the system. This can enable easier viewing of the microplate 500 by a user.

Figure 6:
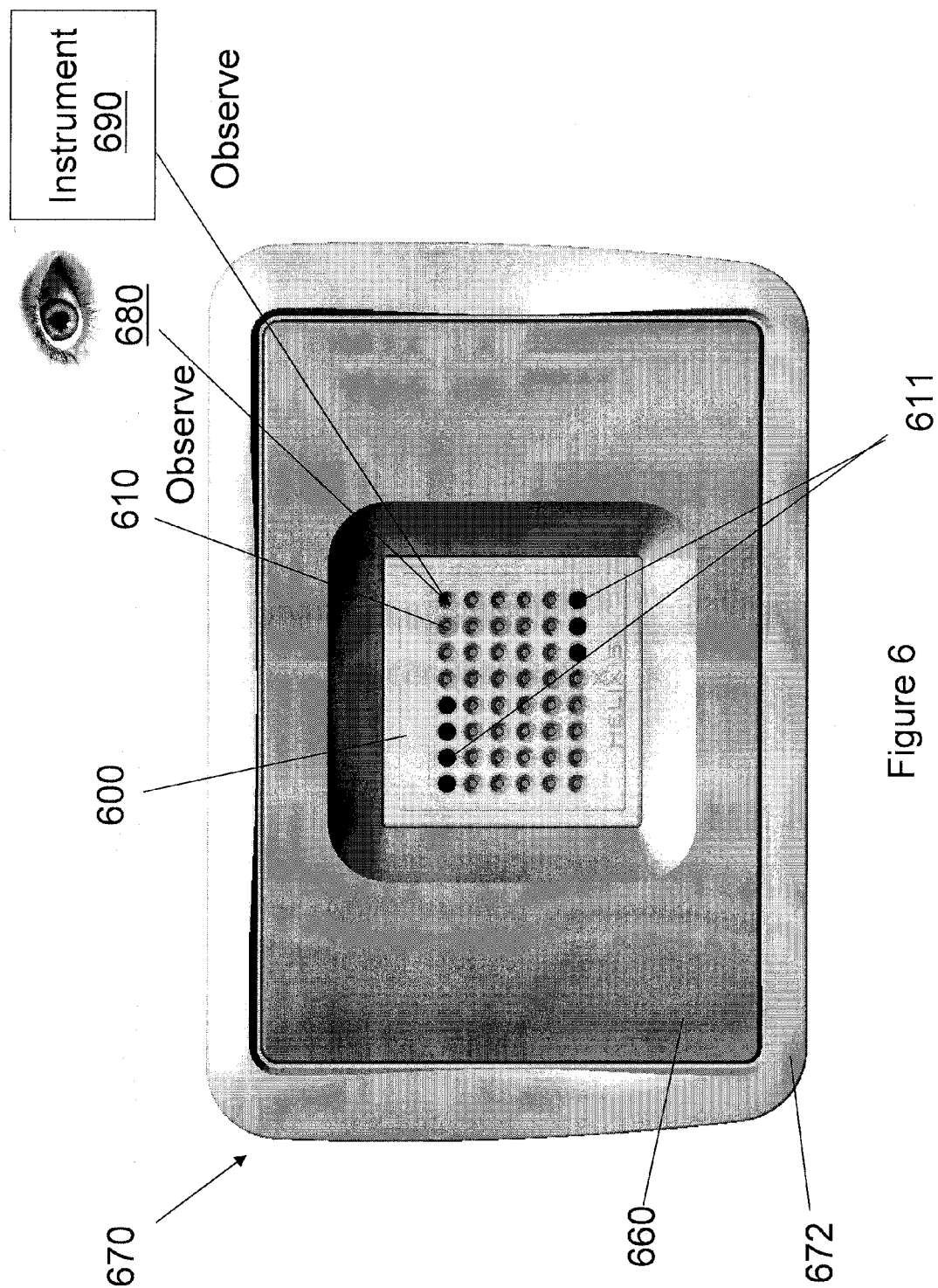
FIG. 6 shows the system of FIG. 5 with the plate, plate holder, and illumination device mated together and viewed from above the plate, through the wells wherein some of the wells have liquid.

FIG. 6 illustrates a system as shown in FIG. 5, wherein the microplate 600 and holder 660 are coupled with or resting on the body 672 of the illumination device 670 of the system. As demonstrated in FIG. 6, the microplate 600 can be illuminated from underneath and the opaque regions of the wells 610 of the microplate 600 provide significant contrast when filled with liquid 611 as compared to a non-filled well 610.

An illumination device can alternatively or in combination comprise a reflective background on which a microplate can rest or be attached to such that the microplate can be illuminated from above the microplate. A reflective background can be any reflective material such as a mirror or a white or a silver surface.

An illumination device can comprise a single light source or a plurality of light sources. For example, an illumination device can comprise a plurality of light emitting diodes (LEDs) wherein, for example, an LED is aligned with one or more wells of the microplate. An illumination device can comprise a single light source. In an example, the illumination device comprises a surface that spreads out the light such as a partially transparent white surface. Additionally, visibility of the opaque region can be enhanced by placing the plate on the illumination surface such that illumination from below generates a controlled brightness level as is programmed by a user or the manufacturer.

In some instances, a system comprises a microplate and a film below the microplate which can be visualized by looking through the wells of the microplate from above, where the film comprises opaque dots or regions corresponding to wells of the microplate. In embodiments having such a film, the microplate generally need not have an opaque region. Here, it is the difference in the visualization fo o of the dots on the film surface which tells the user whether the wells are filled. Where the illumination is provided from below the microplate, the film can be a transparent film with dots corresponding to the places where the wells align with the film. Where the illumination is from above, the film can be opaque, and can be, for example a white or silver surface comprising dots which correspond to each of the wells. The thin film can be a transparent film. In an embodiment, the thin film can be, for example, celluloid paper. In some examples, the thin film is a paper with black or dark colored spots printed on it. The paper can be aligned with the wells of the microplate. The paper can be white or transparent.

In some embodiments, a microplate comprises a thin film coating or coatings in a well to protect the contents of the solution in the reaction chamber from the deleterious effects of the substrate, without compromising the utility of the microplate. The thin film coating can comprise opaque dots that align at the bottom of a well of the microplate.

In many instances, a top surface of the microplate is planar or planar with ridges or protrusions, although other configurations of microplates can be used, for example, concave, convex, three-dimensional, for example spherical, textured, or cavitated top surfaces. The top surface of the microplate typically comprises holes as openings to the plurality of wells within the microplate.

In many instances, a microplate allows optical detection within a well of a chemical reaction and the microplate itself does not appreciably emit light or fluoresce. The substrate can be made of a material that facilitates detection of the chemical reaction event or assay result. For example, in a typical nucleic acid sequencing reaction, binding of a dNTP to a sample nucleic acid to be sequenced can be monitored by detection of photons generated by enzyme action on phosphate liberated in the sequencing reaction. A microplate that is transparent can facilitate detection of the photons. In some embodiments, the substrate is optically transparent.

Microplates can be composed of a variety of materials. Exemplary materials include, but are not limited to, organic polymers and plastics, such as vinyl polymers including polystyrene, polyethylene, polypropylene, polybutylene, polyvinyl chloride, and Teflon®, including copolymers and blends, as well as condensation polymers including polyethylene terephthalate, polyurethanes, polycarbonates, acrylics, polyamides, polyimides, polyesters, and epoxies, and silicones including copolymers and blends. Materials may also include inorganic materials including ceramics, glasses, modified or functionalized glasses, silica or silica-based materials, silicon and modified silicon. Substrate materials may also comprise fiber optic bundles. In an embodiment, the microplate comprises polystyrene. In an embodiment the microplate is transparent, except for the opaque region of a well. In an embodiment, a microplate comprises polypropylene. Polypropylene can have a wide range of temperature stability and can be used for chemical reactions involving a temperature change, such as PCR. Polycarbonate is another material that can be used to manufacture a microplate as described, such that polycarbonate can be inexpensive and easy to mold. In many instances, a microplate is disposable. In some instances, a microplate is reusable.

In an embodiment, a microplate comprises a material with an enhanced thermal conductivity. Examples of materials with enhanced thermal conductivity include, but are not limited, metals, metal oxides, polymers and doped polymers. For example a material with enhanced thermal conductivity can be a plastic, such as CoolPoly.

In some instances, the microplates are sealed, such as heat-sealed with foil or clear film. In an embodiment, a microplate can comprise an embedded layer of filter material or be a solid phase extraction (SPE) microplate. A microplate herein can be used for example in filtration, separation, optical detection, storage, reaction mixing or cell culture.

In some instances, the surface of a well can be modified, for example using a plasma discharge to make it easier for adherent cells to grow within the well. In an embodiment, the modified inner surface of the well can provided a textured surface. In another embodiment, the modified inner surface can provide the opaque region.

In some instances, microplates as described herein are compatible with a robotic microplate handling system.

In an embodiment, a microplate is manufactured by injection molding. The mold can comprise a textured surface as described herein in order to transfer the texture to the microplate. An exemplary molding technique is a Mold-Tech standard (Roehlen Industries, Walnut, Calif.) to manufacture the microplate. Texture can be applied the inner surface of the well is applied to the inner surface of the well opposite the opaque region on the outer surface of the bottom of the well. An exemplary texture mold is texture standard MT-11007 or similar from Mold-Tech.

Other exemplary techniques of manufacturing of a microplate include vacuum forming. In some instances, multiple components of a microplate can be molded separately and later assembled into a finished product. For example, a microplate body can be molded in one step and an opaque region of a well can be molded in another step and they can be assembled together.

A microplate described herein can be a component of a system or utilized in methods as described herein. A system and method can be used to process nucleic acid. For example, methods are performed to determine the identity of a sequence of nucleic acids, or for single nucleotide polymorphism (SNP) detection in nucleic acid fragments, nucleic acid expression profiling, haplotying, karyotyping, or genotyping.

A microplate can comprise a plurality of wells, wherein an individual well of the plurality of wells may receive an aliquot of a sample to be reacted or assays. In the embodiment shown, the microplate includes ninety-six wells arranged in a grid having a plurality of rows and columns. However, the present invention is not limited to this arrangement. The invention can be implemented in any type of microplate arrangement (for example, all established industry standards such as six, twenty-four, forty-eight, ninety-six, or more wells), and is not limited to any specific number of wells or any specific dimensions.

Various biological research and clinical diagnostic procedures and techniques require or are facilitated by a microplate in which multiple samples are disposed for qualitative and quantitative assays or for sample storage and retrieval.

Typically, reactants are distributed into the wells of the microplate in a medium which facilitates the chemical reaction or bioassay. For example, for DNA sequencing, a nucleic acid template can be distributed into a well on one or more solid supports, beads, or particles in a solution.

A microplate herein can contain a number of different reactants and analytes in their reaction chambers. In one embodiment, an individual well of a microplate contains reagents for analyzing a nucleic acid or protein. In one embodiment the nucleic acid species is amplified to provide the desired number of copies using PCR, RCA, ligase chain reaction, or other nucleic acid amplification.

Research techniques that use microplates as described herein include, but are not limited to, quantitative binding assays, such as radioimmunoassay (RIA) or enzyme-linked immunosorbant assay (ELISA), combinatorial chemistry, cell-based assays, thermal cycle DNA sequencing and polymerase chain reaction (PCR), both of which amplify a specific DNA sequence using a series of thermal cycles. Each of these techniques makes specific demands on the physical and material properties and surface characteristics of the sample wells. For instance, RIA and ELISA require surfaces with high protein binding; combinatorial chemistry requires great chemical and thermal resistance; cell-based assays require surfaces compatible with sterilization and cell attachment, as well as good transparency; and thermal cycling requires low protein and DNA binding, good thermal conductivity, and moderate thermal resistance.

Microplates used in thermal cycling procedures can be referred to as thin-well microplates. Microplates herein can be designed to accommodate the stringent requirements of thermal cycling. For example, microplates can be configured to improve thermal transfer to samples contained within sample wells. Sample wells or a microplate can be configured to nest into a heating/cooling block of a thermal cycler, which can increase the surface area of the microplate that is in contact with heating/cooling blocks to improve heating and cooling of samples.

The material of a microplate can be configured to be rigid, strong and/or straight and maintain physical and dimensional stability and integrity during and following exposure to a range of temperatures (for example, 20 to 100° C.).

In an embodiment, a microplate can be run in a thermal cycling apparatus comprising a liquid for rapid temperature changes within a well, such as the thermal cycler in related U.S. Patent Application US 2008/0003649, which is hereby incorporated by reference.

While many embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A microplate comprising: a body and a plurality of wells, wherein each well of the plurality of wells comprises a bottom and a sidewall, wherein the sidewall is at least partially transparent and wherein the bottom comprises an opaque region, and wherein the bottom further comprises an outer surface and a textured inner surface.

2. The microplate of claim 1, wherein the bottoms of the wells each have a substantially horizontal portion, and wherein the opaque region is confined to the substantially horizontal portion.

3. The microplate of claim 1, wherein the plurality of wells are configured to contain a liquid such that when viewed from openings of the plurality of wells, the opaque region has a different appearance for wells containing liquid than for the wells that do not contain liquid.

4. The microplate of claim 1, wherein the textured inner surface of the well scatters less light when in contact with liquid than when the textured inner surface of well is not in contact with liquid.

5. The microplate of claim 1, wherein the opaque region comprises a black dot on the outer surface.

6. The microplate of claim 1, wherein the opaque region is printed onto the outer surface.

7. The microplate of claim 1, wherein the textured inner surface is configured to reflect light from the opaque region.

8. The microplate of claim 1, wherein the textured inner surface is configured to divert light from the opaque region.

9. A system comprising:
a microplate comprising: a body and a plurality of wells, each well of the plurality of wells comprising a bottom, a textured surface, and a sidewall, wherein the sidewall is at least partially transparent and wherein the bottom comprises an opaque region; and
an illumination device configured to receive the microplate such that light from the illumination device passing through the wells of the microplate is scattered by the textured surface, thereby increasing a contrast of a first well of the plurality of wells containing liquid compared to a second well of the plurality of wells not containing liquid.

10. The system of claim 9, wherein the illumination device comprises a body, a light source, and an illumination surface, wherein the light source illuminates the illumination surface and wherein the illumination surface is configured to be positioned under the microplate when received.

11. The system of claim 9 further comprising a holder, wherein the holder is configured to hold the microplate and the illumination device is configured to receive the holder and the microplate.

12. The system of claim 9, wherein the holder is configured to fit into a centrifuge for microplates.

13. The system of claim 9 wherein the textured surface scatters less light when in contact with liquid, thereby increasing a contrast of the opaque region of a first well of the plurality of wells containing liquid compared to a second well of the plurality of wells not containing liquid.

14. A method comprising:
obtaining a microplate comprising a body and a plurality of wells each comprising a bottom and a sidewall, wherein the sidewall is at least partially transparent and wherein the bottom comprises an opaque region;

adding a liquid to at least one of the wells;

observing at least a first well containing liquid and a second well not containing liquid from above the microplate; and determining whether or not liquid has been added to the first well and the second well by comparing a contrast of the opaque region of the first well with a contrast of the opaque region of the second well.

15. The method of claim 14 wherein the observing of the appearance of the opaque region is performed by a person.

16. The method of claim 14 wherein the observing of the appearance of the opaque region is performed by an instrument.

17. The method of claim 14, further comprising illuminating the plurality of wells so as to increase a contrast between the first well and the second well.

18. The method of claim 14, further comprising illuminating a textured inner surface of each of the plurality of wells, wherein liquid in contact with the textured inner surface causes reduced scattering compared to when liquid is not in contact which the textured inner surface.

* * * * *